(12) United States Patent
Slater et al.

(10) Patent No.: US 7,669,484 B2
(45) Date of Patent: Mar. 2, 2010

(54) DEVICE FOR EVALUATING DRAG REDUCTION

(75) Inventors: Kenneth Slater, Houston, TX (US); Mario Zamora, Houston, TX (US)

(73) Assignee: M-I L.L.C., Houston, TX (US)

( * ) Notice: Subject to any disclaimer, the term of this patent is extended or adjusted under 35 U.S.C. 154(b) by 0 days.

(21) Appl. No.: 12/124,919

(22) Filed: May 21, 2008

(65) Prior Publication Data

US 2008/0289435 A1 Nov. 27, 2008

Related U.S. Application Data

(60) Provisional application No. 60/939,500, filed on May 22, 2007.

(51) Int. Cl.
*G01F 1/37* (2006.01)
(52) U.S. Cl. .................................. 73/861.49
(58) Field of Classification Search ........................ None
See application file for complete search history.

(56) References Cited

U.S. PATENT DOCUMENTS

| | | | |
|---|---|---|---|
| 4,734,103 A | | 3/1988 | Fong et al. |
| 5,540,355 A | * | 7/1996 | Hancock et al. ............... 222/56 |
| 5,549,820 A | * | 8/1996 | Bober et al. .................. 210/199 |
| 5,685,161 A | * | 11/1997 | Peckjian et al. ............... 62/149 |
| 6,306,658 B1 | * | 10/2001 | Turner et al. .................. 436/37 |
| 2003/0192693 A1 | * | 10/2003 | Wellington ................. 166/267 |
| 2005/0172631 A1 | * | 8/2005 | Primlani ..................... 60/698 |
| 2007/0090132 A1 | * | 4/2007 | Williams et al. ............ 222/389 |

OTHER PUBLICATIONS

Written Opinion of the International Searching Authority for PCT Application No. PCT/US2008/064473, dated Oct. 24, 2008, (4 pages).
International Search Report for PCT Application No. PCT/US2008/064473, dated Oct. 24, 2008, (3 pages).
Shah, Subhash N., et al. "Drag Reduction Characteristics in Straight and Coiled Tubing: An Experimental Study", Journal of Petroleum Science and Engineering, vol. 53, Sep. 2006, pp. 179-188.
Mowla, D. and Naderi, A., "Experimental Study of Drag Reduction by a Polymeric Additive in Slug Two-Phase Flow of Crude Oil and Air in Horizontal Pipes", Chemical Engineering Science, vol. 61, Mar. 2006, pp. 1549-1554.

\* cited by examiner

*Primary Examiner*—Harshad Patel
(74) *Attorney, Agent, or Firm*—Osha • Liang LLP

(57) ABSTRACT

A system for screening a drag reduction agent that includes at least one pressure vessel, comprising: at least one container having an outlet; a first tube fluidly connected with the outlet of the at least one container; a second tube fluidly connected with the first tube; a timer; and a collection vessel configured to receive a fluid from the second tube is disclosed.

23 Claims, 2 Drawing Sheets

DEVICE FOR EVALUATING DRAG REDUCTION

CROSS-REFERENCE TO RELATED APPLICATIONS

This applications claims priority, pursuant to 35 U.S.C. 119(e) to U.S. Provisional Patent Application No. 60/939,500, filed May 22, 2007. That application is expressly incorporated by reference in its entirety.

BACKGROUND OF DISCLOSURE

1. Field of the Invention

Embodiments disclosed herein relate to comparing the flow rates of two or more fluids. In particular, embodiments disclosed herein relate to comparing the effect of a drag reduction agent in a fluid. More particular still, embodiments disclosed herein relate to screening drag reduction agents to determine whether the drag reduction agent functions as intended according to defined variables.

2. Background Art

Drag reduction is defined as the reduction of a fluid's frictional resistance in turbulent flow and thus increase in pumpability of the fluid caused by the addition of small amounts of another substance, frequently high molecular weight polymers, to the fluid. Specifically, drag reduction is a reduction in the pressure drop over some length of a pipeline when traces of a drag reduction agent are dissolved in the pipeline fluid. The key factors governing the amount of drag reduction achievable in a given system are: solubility of the agent in the continuous phase; effectiveness in dispersing the agent; molecular weight of the agent; and concentration of the agent. The phenomenon of drag reduction has been used in a variety of pipelines to reduce shear stresses and thereby decrease the amount of pump power input necessary to flow fluids therethrough.

When fluids travel through a pipe, a velocity profile develops that varies from zero velocity (at the wall of the pipe) to a maximum velocity (at the centerline of the pipe). This profile is caused by viscid flow properties that create shear layers in the fluid. At very low bulk flow velocities, these shear layers are well-ordered laminae, and there is no transverse flow between the layers, which is described as laminar flow. Pressure drop per unit length of pipe is also low. As bulk flow velocities increase, the laminar nature of the flow begins to break down. At the interface between laminae, the local flow begins to tumble due to shearing, creating transverse flow, in which faster moving particles are transported into regions of lower velocity and vice-versa. This turbulent flow causes greater pressure drop per unit length of pipe and demands higher pumping energy into the flow to maintain the bulk velocity of the flow.

These two flow regimes are defined by Reynolds number (Re), the ratio of the fluid body forces to viscous forces. Values of Re of less than 2000 include the laminar flow regime for pipes. As Re increases, pipe flow transitions from laminar to turbulent over a range of values from 2,000 to 10,500 and is fully turbulent above 10,500. Typically, drag reducers are very high molecular weight hydrocarbon polymers suspended in a dihydrocarbon solvent. When added to crude or refined products in a pipeline, these polymers reduce transverse flow gradients, effectively creating a laminar flow in the pipe. This is especially true close to the pipe walls where the axial flow velocity profile has a very steep gradient in which significant pressure losses occur. Lowering these internal fluid losses increases the bulk throughput of the pipeline for a given pumping energy.

Typically, the amount of drag reducer in a fluid is small, on the order of one part per million. The drag reducer molecular chain is very fragile, however. The chain can be sheared or broken as the chain passes through both natural and/or man-made features, such as bends in a pipeline, valves, piping branches, and when the flow goes through a pumping station. Thus, the chain may be broken by passage through any type of stream. Once the molecular chain is broken, the drag reducer is immediately degraded. The extent of drag reduction is limited by this degradation of drag reducing agents into smaller, less-effective chains as the polymers travel downstream. It has been show that the rate of this degradation is strongly dependent on diameter. As industrial pipelines are often orders of magnitude larger than laboratory-scale pipelines, diameter is an important consideration in industrial pipeline scale-up. For example, as pipeline diameter increases from that of fire hoses (50 mm) to the Trans-Alaska Pipeline System (1194 mm), operating at the same wall shear stress of approximately 40 Pa, the apparent first-order rate constant for polymer degradation decreases by three orders of magnitude.

In dilute solution, non-ionic vinyl polymers, such as polyethylene oxide, form random coils independently of one other. In turbulent flow, it is theorized that the polymer chains extend to bridge turbulent "bursts," thereby decreasing turbulence production and thence, presumably, the wall shear stress. For example, turbulent jets of water and polyethylene oxide solution were compared to show that the polymer chains suppressed small-scale eddies.

In 1970, a series of experiments measured drag reduction at different Reynolds values and concentrations. It was discovered that, for low turbulent Re, as the concentration of polymer increases, the friction coefficient decreases, thus implying an increase in drag reduction. It was also shown that drag reduction was linearly correlated to concentration for concentrations below 50 ppm, suggesting that the polymer chains work independently of one another to cause drag reduction.

Drag reduction efficiency has also been strongly correlated with the molecular weight of the polymer. At higher molecular weights, the onset of drag reduction begins at lower Reynolds number values. For this reason, high molecular weight polymers have been favored for commercial applications. Experiments with polyethylene oxide also support the requirements of long molecules of high molecular weight, with few side branches and good solubility as ideal polymers for drag reduction.

The injection of long-chain polymers into pipe flow is the most widely-studied and commercially applicable form of drag reduction. Drag reducers are often used in pipeline systems to facilitate the flow of crudes, diesel fuels, and automotive gasoline, and are also used in the formulation of thixotropic fluid systems used in wellbores. The amount of drag reduction agent required in ppm to achieve a certain flow increase depends upon many factors. For a particular pipeline, depending upon the liquid viscosity and gravity and the Reynolds number, drag reduction effectiveness effectiveness varies with flow rate.

Currently, the definitive apparatus used for testing drag reduction is a flow-loop test, the results of which can be scaled-up to a full-scale pipe, otherwise known as a scale-up flow loop ("SUFL"). A SUFL is built from small-diameter conduits to limit laboratory space and fluid volumes, and is used to predict frictional pressure losses for the same fluid in large-diameter conduits and precisely determine the drag reduction of a fluid and/or a fluid additive. Flow-loop and sectional geometry include the length, hole diameter, and external and internal pipe diameters, respectively. Flow loops are considered to have a singular geometry, although some are configured with serial and parallel test sections of different diameters.

As fluid density and rheological properties are maintained constant during SUFL testing, the fluid temperature should not vary appreciably during the entire test procedure. Thus, for flow-loop experiments, test-section geometry and mud properties do not change. To calculate pressure losses in a pipeline or well, the fluid passes through depth intervals (or section lengths) at a constant flow rate. For a wellbore, drill string and annular pressures would be the summation of the calculated pressures in each row for different flow-rate values.

While SUFL testing may produce accurate drag information, the preparation and operation requires significant investments of time and money. First, the SUFL typically requires five-gallon sample of testing fluid, which could be costly depending on the cost of the fluid and/or the additive. Additionally, one test-run lasts about 1 hour per sample. Once a sample fluid is tested, the system must be flushed of all remaining fluid to prepare for the next test sample, adding additional time to the testing process. Economic shortcomings also derive from the high cost of energy required for the operation and cleaning of the SUFL, as well as the high cost of parts required to assemble a SUFL. Due to the increasing costs of producing, testing, and implementing wellbore fluids, the industry needs a streamlined testing system and method that uses less energy, sample volume, and time.

Accordingly, there exists a continuing need for an effective test to measure the impact on drag by drag reduction agents.

SUMMARY OF INVENTION

In one aspect, embodiments disclosed herein relate to a system for screening a drag reduction agent that includes at least one pressure vessel, comprising: at least one container having an outlet; a first tube fluidly connected with the outlet of the at least one container; a second tube fluidly connected with the first tube; a timer; and a collection vessel configured to receive a fluid from the second tube.

In another aspect, embodiments disclosed herein relate to a method for measuring a drag reduction agent that includes pressurizing a pressure vessel comprising at least one container having a fluid therein; conveying the fluid through a first tube; conveying the fluid though a second tube; collecting the fluid exiting the second tube in a collection vessel; and measuring a flow rate of the fluid through the first and second tube.

Other aspects and advantages of the invention will be apparent from the following description and the appended claims.

DETAILED DESCRIPTION

In one aspect, embodiments disclosed herein relate to measuring the flow rates of fluids. In another aspect, embodiments disclosed herein relate to measuring the friction factor of fluids at a constant pressure. In particular, embodiments disclosed herein relate to measuring the effect of a drag reduction agent in a fluid. More specifically, embodiments disclosed herein relate to measuring the effect of a drag reduction agent in a wellbore fluid.

Those of ordinary skill in the art will appreciate that being able to determine whether a drag reduction agent works according to specified conditions may allow for the selection of an optimal drag reduction agent. Additionally, embodiments disclosed herein may allow an operator to perform an initial test of multiple drag reduction agents, so that the operator may determine whether more extensive, and thus more expensive tests should be performed. Thus, in certain embodiments, the apparatuses and methods disclosed herein may be used in performing an initial drag reduction agents screening to determine general effectiveness, while in other operations, the apparatuses and methods disclosed herein may be used in determining optimal drag reduction agent properties for a given condition.

Figure 1:
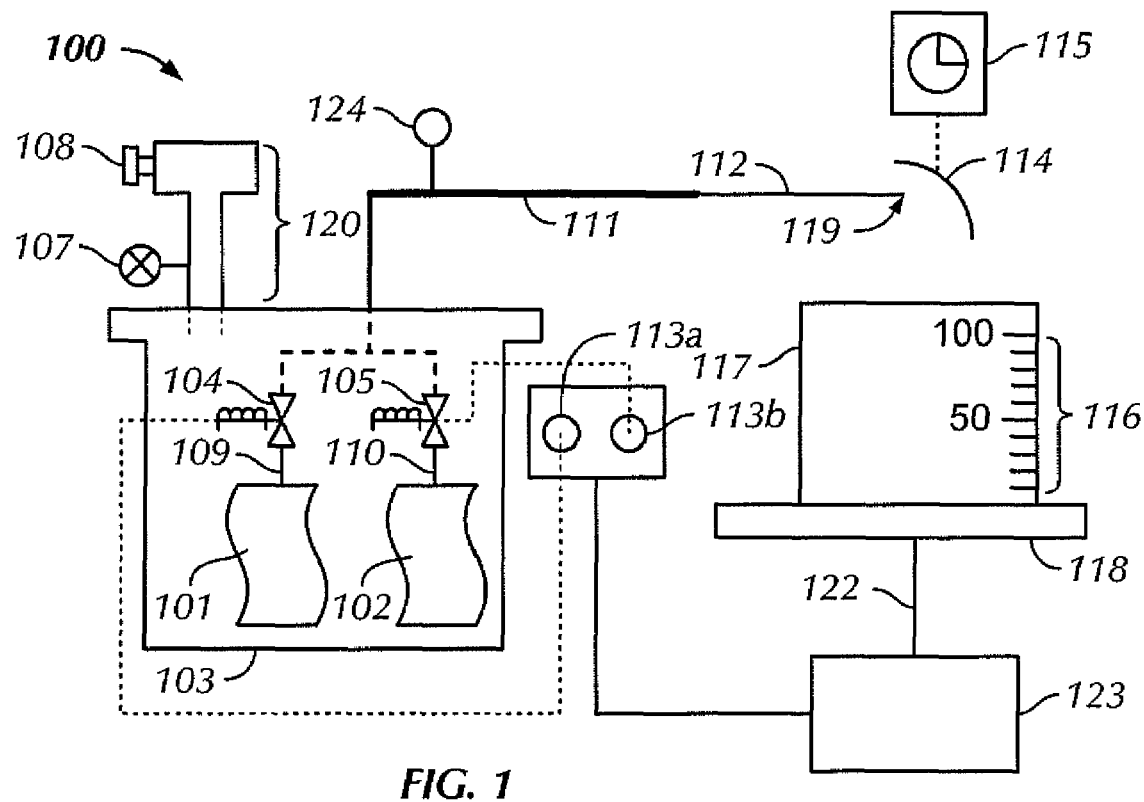
FIG. 1 is a schematic of one embodiment of the present disclosure.

Referring to FIG. 1, a schematic of a system 100 according to one embodiment of the present disclosure is shown. In this embodiment, two containers 101, 102 are located inside a pressure vessel 103. The containers 101, 102 may include any collapsible or compressible, non-reactive container, such as those made of pliable plastic or rubber. One example of a container may include a NALGENE® narrow-mouth sample bag, commercially available from NALGENE® Labware. Container 101 may, for example, contain therein a control fluid, such as water, a brine solution, or base oil. Control fluid, as used herein, means any fluid that does not contain an additive of interest to the testing procedure. The second container 102 may contain, for example, a test fluid. Test fluid, as used herein, means any fluid that contains an additive, such as a drag reduction agent, of interest to the testing procedure. One of ordinary skill in the art will appreciate that the control fluid and the test fluid may contain other additives that are not the subject of the test. In one embodiment, the fluid formulas contained in the different containers will differ by one additive or additive concentration. This will limit the variables in the measurements, as well as provide comparisons of a variety of fluid formations.

Each container 101, 102 is equipped with an outlet 109, 110, respectively. One of ordinary skill in the art would appreciate that outlets 109, 110 may be configured so as to enable a rapid change in flow of fluid out of or between each container. As shown, each outlet 109, 110 is fluidly connected to a valve 104, 105, respectively. As shown in the embodiment of FIG. 1, valves 104, 105 are solenoid valves. However, in other embodiments, valves 104, 105 may include other mechanical or electrical devices known in the art, such as actuators or other latching mechanism. Both valves 104, 105 are fluidly connection to a first tube or load tube 111. The first tube 111 may include any type of tube, such as flexible tubes, coiled tubes, smooth tubes, straight tubes, or other tubing known in the art of fluid testing. One end of the first tube 111 is within pressure vessel 103, and the other end is located outside pressure vessel 103. This may be facilitated by the placement of a hole on surface of pressure vessel 103, which is fitted and sealed to the first tube 111 so that the first tube 111 may pass through pressure vessel 103 while still retaining constant pressure inside pressure vessel 103. One of ordinary skill in the art will appreciate the various means for passing a tube through a vessel, and sealing the area between the outside of the tube and the vessel, so as to prevent gas from flowing in or out of the vessel.

Pressure vessel 103 may be coupled with a pressurization system 120. The pressurization system 120 may include a pressure relief valve 108, a pressure gauge 107, and a pressure source (not shown), such as a compressor. In one embodiment, a pressure regulator (not shown) may be operatively connected to an air flow line from the pressure source to regulate the pressure inside the pressure vessel 103.

Still referring to FIG. 1, the first tube 111 is fluidly connected to a second tube 112 or measurement tube. The second or measuring tube 112 may include any type of tube, such as flexible tubes, coiled tubes, smooth tubes, straight tubes, or other tubing known in the art of fluid testing. Generally, the first tube 111 and the second tube 112 may be of a cylindrical shape. However, one of ordinary skill in the art would appreciate the type of tubing used for the first tube 111 and the second tube 112 may depend on a variety of factors, such as, the space available for the test. For example, coiled tubing requires less space than a straight tube of the same length. One of ordinary skill in the art will recognize that mathematical adjustments to collected data may be required with certain tube geometries. When sizing the first tube 111 and second tube 112, one of ordinary skill in the art would appreciate that the objective may be for the pressure loss in the first tube 111 to be insignificant compared to that of the second tube 112. In one embodiment, the first tube 111 may merely be a means for conveying the test fluid to measuring tube 112.

In one embodiment, the inner diameter of the second tube 112 is 10% to 50% smaller than the inner diameter of the first tube 111. In another embodiment, the inner diameter of the second tube is 10% to 40% smaller than the inner diameter of the first tube 111. In yet another embodiment, the inner diameter of the second tube 112 is 10% to 20% smaller than the inner diameter of the first tube 111.

In one embodiment, the system may include a timer 115. As shown in FIG. 1, the timer is coupled with a deflector 114 and the second tube 112. The deflector 114 is positioned proximate to an outlet 119 of the second tube 112. The timer 115, the second tube 112, and the deflector 114 may form an open circuit. The deflector may be curved, however, one of ordinary skill in the art will appreciate the various deflector designs available in the industry. Additionally, timer 115 may be operatively connected to one or more buttons, such that timer functions may be controlled therefrom.

In another embodiment, the deflector 114 is located above a collection vessel 117. Collection vessel 117 may include any type of vessel used to hold fluids, including steel or plastic containers. In FIG. 1, the collection vessel 117 is illustrated as an open vessel below the deflector plate, however, the location of the collection vessel may also include under the outlet 119, or any location wherein a fluid flowing through the second tube 112 may be collected in the collection vessel 117. The collection vessel 117 may include a volumetric scale 116 and a weight sensor 118. In this embodiment, the weight sensor 118 is illustrated as a scale and is disposed so that it measures the weight of the collection vessel 117 and any contents in the collection vessel 117. The weight sensor 118 may include any device used to measure weight. The weight data is collected by weight sensor 118 then transferred via data line 122 to a programmable logic controller ("PLC") 123. In alternate embodiments, data from weight sensor 118 may be transferred to PLC 123 via wireless communication equipment known to one of ordinary skill in the art. Alternatively, the weight may also be manually recorded.

PLC 123 may include a number of input and output means, display devices, and communication/calculation packages. In one embodiment, PLC 123 includes a receiving input (not shown) for receiving data from weight sensor 118 and a display unit (not shown) for displaying the results of data calculated from at least weight sensor 118. The display unit may include a graphical user interface ("GUI") rendered by instructions provided from the PLC or an associated computer Furthermore, the input device and the display unit may interface directly such that data may be input to PLC 123 via, for example, a touch screen or another input type as known to those of ordinary skill in the art.

The system 100 may include a plurality of sensors that may be used to measure, inter alia, pressures, temperatures, densities, flow rates, flow levels, fluid weight (as discussed above) or other parameters of the system 100 or of fluids being tested. Also, sensors may be located at several points in the system 100. For example, in the embodiment shown in FIG. 1, a pressure sensor 124 is coupled with the first tube 111 to measure the fluid pressure in the first tube 111. Thus, sensors may be used to collect data or to determine a condition at multiple points in the system 100. In one embodiment, sensors may be operatively connected to data acquisition system. Data acquisition system may include any device used to collect, document, or analyze data from the system 100. Examples of data acquisition systems that may be used in aspects of the present disclosure include the PLC 123, analog-to-digital converters, and digital-to-analog converters. Thus, embodiments in certain embodiments, data acquisition system may receive a digital and/or analog input/output from sensors, or directly from another component of the system 100, collect and/or analyze the data, and in certain embodiments, transfer the data to a computer (not shown) for further analyzing. Examples of methods of transferring the data from the data acquisition system to a computer may include, for example, via a USB (universal serial bus), parallel ports, serial communication ports, direct data acquisition plug-in boards, or remote terminal connections. Thus, in certain embodiments, data acquisition system may be directly or indirectly configured to transfer data to computer.

In one embodiment, the system 100 measures the flow rate of a fluid and/or compares the flow rates (and drag reduction) of two or more fluids to each other. Containers 101, 102 may be partially-filled or fully-filled with test fluids or control fluids. As discussed above, one of ordinary skill in the art will appreciate that the fluid in container 101 may be a different formulation than the fluid in container 102. Generally, one of the fluids may be a control fluid, including water, brine, or base oil solution. In one embodiment, the formulation of the fluid in container 101 and the formulation of the fluid in container 102 only vary by one additive. One of ordinary skill in the art will appreciate that both containers do not have to contain a fluid since each container is tested independently of the other one.

Still referring to FIG. 1, the operation of a system of the present disclosure is discussed. As shown, container 101, contained within pressure vessel 103, holds a fluid, wherein the fluid includes an additive that will be tested in the system 100. The additive may include any additive used in the reduction of drag or fluid friction such as, for example, graphite, synthetic polymers, and molybdenum disulfide. In one embodiment, the pressurization system 120 increases the pressure inside the pressure vessel 103 to a driving pressure, which may, in one embodiment, be about 50 psi. However, in other embodiments the pressure may range from 1 psi to 200 psi, depending on operational and testing conditions. One of ordinary skill in the art will appreciate that the pressure may also vary depending on ambient conditions, pressure rating of the equipment, as well other system variables. One of ordinary skill in the art will also appreciate that the pressurization system 120 may be controlled manually via pressure relief valve 108, pressure gauge 107, a precision regulator (not shown), or by PLC 123. As discussed above, PLC 123 may set and control the testing conditions, such as the pressure inside the pressure vessel 103.

Once the pressure vessel 103 reaches the driving pressure, valve 104 changes from a closed position to an open position via a switch 113A. Switch 113A may be controlled via data acquisition system, PLC 123, manually, or other means of actuation known in the art. The pressure vessel 103 compresses the container 101 at a substantially constant driving pressure. Thus, as the substantially constant driving pressure compresses the container 101, the fluid contained therein will flow at a substantially constant rate through outlet 109 and into the first tube 111. Briefly referring to container 102, one of ordinary skill in the art will appreciate that container 101, outlet 109, switch 113A, and valve 104 possess an analogous configuration to container 102, outlet 110, a switch 113B, and valve 105. In the embodiment shown, the same process may be independently, but not simultaneously, performed with container 102, outlet 110, switch 113A and valve 105.

As discussed above, the fluid is loaded into and flows through the first tube 111 for delivery into the second tube 112 for fluid flow measurement. Further, while the first tube 111 and second tube 112 may be referred to as the load tube and measurement tube, respectively, one of ordinary skill in the art would appreciate that some fluid flow measurements may also be taken in first tube 111.

In one embodiment, the transition from the larger inner diameter of the first tube 111 to the smaller inner diameter of the second tube 112 may induce a turbulent flow in the fluid. However, fluid characteristics, including polymer concentration and viscosity, as well as tubing characteristics, such as the percent difference of the inner diameters, may affect turbulent flow transition. In one aspect of one embodiment, turbulent flow may be necessary for reliable test data. However, one of ordinary skill in the art would appreciate that turbulent flow may also be induced using other ways known in the art, including baffles.

As the fluid flows through the second tube 112, the fluid pressure will drop as the fluid moves the length of the second tube 112. One of ordinary skill in the art will appreciate that the flow of the fluid should be fully developed, i.e., turbulent, prior to entering the second tube 112. An inadequate fluid flow, i.e., laminar, may cause a high, inaccurate pressure drop through the second tube 112. This inaccuracy could lead to biased test results and mask the effect of a drag reduction agent.

In one embodiment, the fluid flows through the second tube 112 and through the outlet 119. In this embodiment, once the fluid passes the outlet 119, it contacts the deflector 114, thus, closing the circuit between the deflector 114 and the timer 115. Once the circuit is closed, the timer begins measuring the time. The timer 115 will continue to measure the time until the fluid ceases contact with the deflector 114, thereby breaking the circuit. The time may be recorded for use in subsequent calculations, such as, determining flow rate or fluid velocity. In another embodiment, time measurements may be provided manually via a stopwatch, by a PLC, or other automated devices. Further, one of ordinary skill in the art would appreciate that from the flow rate, and other known characteristics, such as fluid rheology, and system specifications, additional calculations may be performed, such as calculation of fanning friction factor, frictional pressure loss, and Reynolds number. In certain embodiments, timer 115 may be manually controlled through one or more switches, buttons, or other components capable of allowing for the control of timer 115.

As discussed above in FIG. 1, the deflector 114 is positioned above the collection vessel 117. The deflector 114 directs the fluid velocity to the opening of the collection vessel 117. The collection vessel 117 may comprise the volumetric scale 116 to provide a visual volume measurement of the fluid in the collection vessel 117. However, the fluid volume may be measured by other devices, including automated devices, graduated cylinders and volumetric displacement methods. After the fluid no longer flows into the collection vessel 117, a final volume measurement is recorded manually or in an automated data collection system.

The weight sensor 118 measures the weight of the fluid collected in the collection vessel 117. In one embodiment, the weight is recorded after the fluid stops flowing into the collection vessel 117. However, the weight may be recorded at regular intervals during fluid collection. The weight may be recorded manually, or, as illustrated in FIG. 1, the weight data may be communicated via line 122 to the PLC 123. Although the weight sensor 118 is coupled with the collection vessel 117, one of ordinary skill in the art will appreciate that the weight sensor may also be independent from the collection vessel 17.

Although FIG. 1 shows two containers 101, 102 in pressure vessel 103, one of ordinary skill in the art will appreciate that the system 100 may have one or more containers in a pressure vessel, as shown below in FIG. 2. One of ordinary skill in the art will also appreciate that the system 100 can have multiple pressure vessels, each having one or more containers therein. Further, another alternate embodiment may include one or more pressure vessels, each containing one or more containers therein, where each container may be fluidly connected to its own load and measurement tubes. With multiple tubing connected to one or containers in one or more pressure vessels, one of ordinary skill in the art would appreciate that the testing may be done simultaneously or sequentially. If testing is to be performed simultaneously through two or more load and measurement tubes, one of ordinary skill in the art would also appreciate that multiple collection vessels, etc. may be used to collect data simultaneously.

Moreover, one of ordinary skill in the art will appreciate that the system 100 can have multiple pressure vessels and multiple tubing connected to one or more switches. The number of containers, pressure vessels, and tubing used in the system 100 will depend on multiple factors, such as, for example, the number of testing fluids, fluid properties, and spatial limitations, as described above.

Figure 2:
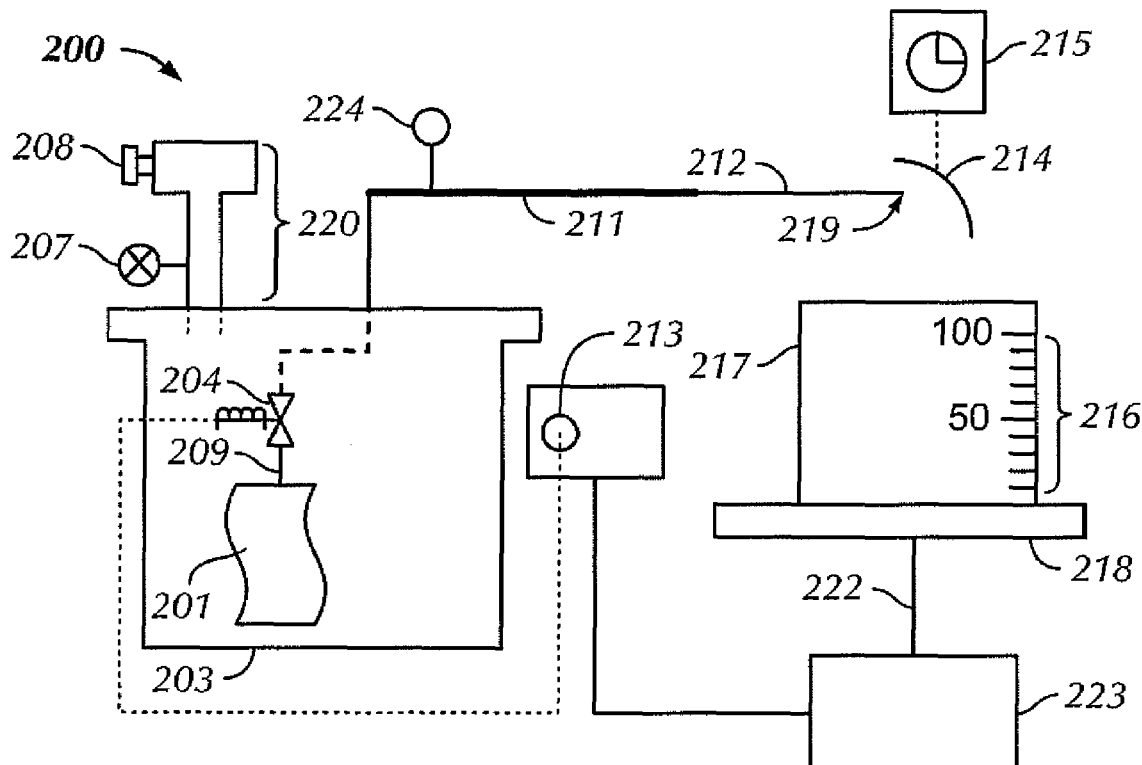
FIG. 2 is a schematic of one embodiment of the present disclosure.

Referring to FIG. 2, an alternate schematic of a system 200 having a single container 201 contained within pressure vessel 203 is shown, where like numerals represent like components. In this embodiment, a single container 201 is located inside a pressure vessel 203, which may be pressurized via pressurization source 220. Container 201 is fluidly connected to first tube 211 and second tube 212. In operation, when fluid loads into first tube 211 and passes through tube 212, it is collected in collection vessel 217.

Principles and Theory

As described above, fluid flow is characterized as being either laminar or turbulent. In laminar flow the fluid moves in layers, with one sliding smoothly over the other. There is no mixing of fluid from layer to layer, since viscous shear forces damp out relative motions between layers. Since each layer of fluid is in effect flowing over the one adjacent to it, the fluid velocity increases with the distance from the pipe wall. The resulting velocity profile is approximately parabolic in shape.

In turbulent flow, there are no discrete layers of flowing liquid. The momentum of the fluid overcomes the viscous shear forces, and there is extensive and continual mixing across the flow stream. This causes the velocity profile across a pipe to be nearly flat. In fluid dynamics, turbulent flow is characterized by rapid fluctuations of properties such as velocity, pressure and shear stress as a function of time and position in the flow. These fluctuations lead to high momentum convection and the production of unsteady vortices or eddies which lead to an increase in skin friction. This increase in drag has implications in design of piping systems where the energy required for pumping turbulent fluids increases considerably relative to laminar flow.

Adding small quantities of material, such as high molecular weight polymers, to a fluid in turbulent flow could considerably reduce frictional drag exerted by the fluid when it flows over a surface such as a pipeline. This phenomenon is referred to as polymer turbulent drag reduction. The most striking application of this behavior is reduction in pumping energy requirements for pipeline flow. Drag reduction is not only important from an application point of view but also from a fundamental viewpoint. Understanding the mechanism of drag reduction will also provide insight into the phenomenon of turbulence, a very complex entity in itself.

Polymers are long chain molecules of typical dimension about 10-100 nm. When added in dilute concentrations to fluids, they reduce friction drag in pipes by as much as 20% to 80%. The origin of the drag reduction mechanism is the stretching of polymer molecules in a turbulent flow. This stretching dampens turbulent fluctuations and reduces drag. Thus, the extent of drag reduction is a function of the size of the polymer (governed by its molar mass) and the number of polymer molecules (governed by the polymer concentration). An aspect of embodiments of the present disclosure provide the measurements necessary to test the relationship between friction drag and molecular properties of an additive, such as its concentration, by measurement of flow rate and pressure drop.

Friction drag behavior is typically correlated as friction factor as a function of a fluid's Reynolds number. The following equations illustrate this relationship:

$$\Delta P = \frac{2f\rho U_{av}^2 L}{d} \quad (1)$$

Where:
ρ=fluid density
ΔP=pressure drop across the second tube,
f=fanning friction factor,
d=diameter of the second tube,
$U_{av}$=mean fluid velocity in the flow direction averaged across the second tube's cross section,
L=Length of the second tube.

$$\tau_w = \frac{\Delta P d}{4L} \quad (2)$$

where
$\tau_w$=wall shear stress.

The Reynolds number is:

$$Re = \frac{dU_{av}}{v_s} \quad (3)$$

where:
$v_s$=kinematic viscosity of the fluid.

The Fanning Friction Factor is:

$$f = \frac{2\tau\omega}{\rho U av}$$

The relationships above are especially useful in turbulent flow regimes. In evaluating the friction factor, one of ordinary skill in the art will appreciate that the same data may be plotted using other relationships, such as Prandtl-Karman coordinates, wherein the wall shear stress is below a critical value and, therefore, no drag reduction exists in a Newtonian solvent in turbulent flows.

Generally, drag reduction additives increase local viscosity, thereby dampening the small eddies created by the turbulent flow, and increasing the thickness of the viscous sublayer. With a thicker sublayer at the same total flow, the pressure drop for the length of the second tube is lower than a fluid without the drag reduction additive. Therefore, fluids with drag reduction additives require less energy to flow through pipes.

Testing multiple pressures using wellbore fluid pairs may be especially useful in type-curves analysis. Type curves are families of paired pressure changes and their derivatives, computed from a model. The model is usually generated from an analytical solution of the diffusion equation with boundary conditions strategically defined to enable observation of theoretical trends in the pressure-transient response. The boundary conditions that can be defined near the well include constant or variable wellbore storage, limited entry (partial penetration), radial composite (damage skin due to permeability alteration), and a fracture extending the cylindrical wellbore to a extended plane. The borehole trajectory can be vertical, angled, or horizontal. The distant boundary conditions include a sealing or partially sealing planar boundary (fault), intersecting faults and rectangular boundaries (sealing or constant pressure). Further, the diffusion equation can be adjusted to accommodate reservoir heterogeneity in the form of dual porosity or layering. Finally, when generated with computer assistance, the type-curve family can account for superposition in time due to flow-rate variations before and even during the transient data acquisition. When a match is found between data and a type curve, the parameters that characterize the behavior of the model providing a match are thereby determined. Thus, comparisons may be made across a matrix of drag reducers without the complication of setting exact pressures.

TEST EXAMPLES

In some embodiments, the present disclosure provides a system and a method for a comparison between multiple fluids using single sample loading for each fluid, in that each fluid sample may be loaded at one time into multiple containers. The following examples were used to test two fluids of varying additives, concentration, and/or viscosity.

Example Test 1

In test 1, two fluids, Fluid A and Fluid B, were tested using one of the embodiments of the present disclosure. A first container held Fluid A while a second container held Fluid B. A pressure vessel provided a driving pressure of 30 psi via a pressurization system. A switch opened a valve between the container and a first tube, and Fluid A flowed into the first tube. The test was repeated using two additional driving pressures, 40 psi and 50 psi, for Fluid A. Once the test results were compiled for Fluid A, the test was repeated using Fluid B at the three driving pressures, 30 psi, 40 psi, and 50 psi. When the fluids entered the second tube, they possessed a turbulent flow regime, as evident from the Reynolds numbers in Table 1, i.e., the Reynolds numbers are above 3000.

The data in Table 1 reflects test results using a second tube with an inner diameter of 0.09 inches and a length of two feet. Both fluids reached turbulent flow at all three driving pressures, therefore the results may be reliable for purposes of test analysis.

As discussed above, the flow rate may be used to calculate additional fluid properties for evaluating drag reduction.

Similarly, the data collected during the tests for Fluid B are detailed below in Table 3:

TABLE 3

Example Test 2 Data

| Test | Average Pressure (psi) | Time (min) | Tare (g) | Tare + Fluid (g) | Fluid (g) | Flow (mL/min) |
|---|---|---|---|---|---|---|
| 1 | 19.9 | 5.967 | 122.47 | 247.23 | 124.76 | 1254.50 |
| 2 | 19.9 | 7.172 | 121.02 | 271.06 | 150.04 | 1255.21 |
| 3 | 29.9 | 5.225 | 122.34 | 266.94 | 144.60 | 1660.48 |
| 4 | 29.9 | 5.905 | 128.92 | 163.54 | 163.54 | 1661.71 |
| 5 | 49.8 | 3.802 | 124.44 | 270.87 | 146.43 | 2310.84 |

Figure 3:
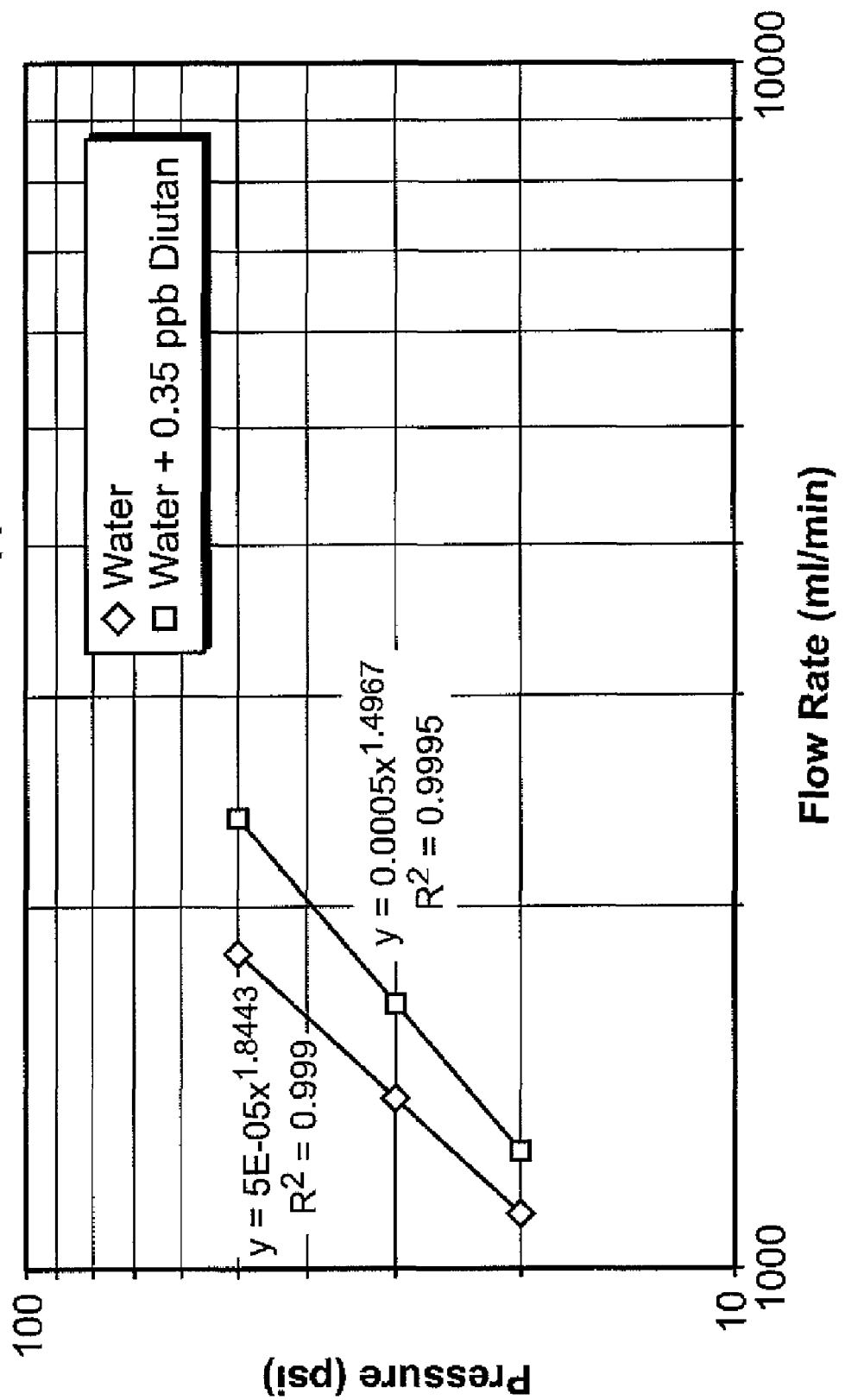
FIG. 3 is a graphical representation of data collected according to one embodiment of the present disclosure.

As is illustrated by the above data, the average flow of Fluid A was 1111.0 (mL/min) at 19.8 (average psi), 1400 (mL/min) at 29.8 (average psi), and 1823 (mL/min) at 49.8 (average psi). For fluid B, the average flow was 1255 (mL/min) at 19.9 (average psi), 1661 (mL/min) at 29.9 (average psi), and 2311 (mL/min) at 49.8 (average psi). The results are displayed in graphical form in FIG. 3. After collection, such data may be

TABLE 1

Example Test 1 Data

| Fluid | Testing Parameters | | | Pressure (psi) | | |
|---|---|---|---|---|---|---|
| | | | | 30 | 40 | 50 |
| A | Inner Diameter (inches) | 0.09 | Re | 3907 | 4602 | 5234 |
| | Length (feet) | 2 | | | | |
| | Viscosity (cP) | 4 | Avg. Flow Rate | 0.371 | 0.437 | 0.497 |
| | Concentration (ppg) | 10 | (gpm) | | | |
| B | Inner Diameter (inches) | 0.09 | Re | 17189 | 20247 | 23024 |
| | Length (feet) | 2 | | | | |
| | Viscosity (cP) | 1 | Avg. Flow Rate | 0.489 | 0.576 | 0.655 |
| | Concentration (ppg) | 8.34 | (gpm) | | | |

Example Test 2

Test 2 included testing Fluid A, water, and Fluid B, water and 0.35 parts per billion Diutan. A first container held Fluid A, while a second container held Fluid B. A pressure vessel providing average pressures of 19.9 psi, 29.8 psi, and 49.8 psi drove each fluid through the test apparatus. The data collected during the tests for Fluid A are detailed below in Table 2:

TABLE 2

Example Test 2 Data

| Test | Average Pressure (psi) | Time (min) | Tare (g) | Tare + Fluid (g) | Fluid (g) | Flow (mL/min) |
|---|---|---|---|---|---|---|
| 1 | 19.8 | 8.507 | 122.47 | 280.08 | 157.61 | 1111.63 |
| 2 | 19.8 | 7.368 | 121.02 | 257.28 | 136.26 | 1109.61 |
| 3 | 29.8 | 6.064 | 122.34 | 263.85 | 141.51 | 1400.16 |
| 4 | 29.8 | 5.838 | 128.92 | 265.17 | 136.25 | 1400.31 |
| 5 | 49.8 | 4.432 | 121.02 | 255.71 | 134.69 | 1823.42 | used in selecting drag reduction agents for a particular operation. Similarly, graphical representations of the collected data, such as FIG. 3, may be useful in selecting a drag reduction agent or otherwise determining such agents are not needed in a given operation.

Advantageously, embodiments disclosed herein may provide a system and method for testing drag reduction agents in fluids. Embodiments disclosed herein may advantageously provide for the use of small sample volumes, low voltage, and low fabrication costs. Furthermore, embodiments disclosed herein may advantageously provide for single sample loading, thereby reducing total testing time. Single-sample loading provides for a streamlined testing system and method since the tests may be performed without costly delays between samples. Current fluid drag tests require time to clean the testing devices between samples. However, embodiments disclosed herein provide a system and method for loading two independent samples at one time, avoiding cleaning in between two tests.

Other advantages may include the use of collapsible containers that minimize the mechanically degradation/shearing of the long chain polymers as the pumps in the SUFL tend to do. Also, since a test fluid may be passed through the measurement tube only once, degradation of the long chain poly mers due to recirculation may be minimized. This lack of circulation may also minimize any temperature effects during the test. Further, with the use of the collapsible containers, a constant pressure may be applied to the fluid.

Further, by using the methods and systems of the present disclosure as a screening tool, multiple fluids may be compared in a relatively short amount of time, as compared to traditional tests. Following screening of various test fluids, a recommendation may be made to undergo additional testing, such as in SUFL. Thus, in certain embodiments, the present disclosure may be used as a cost-effective pre-screening system for testing drag reduction agents prior to testing by more costly procedures. Fabrication of certain embodiments may require materials that are readily available and low in cost.

By providing a relative comparison between neat fluids and fluid with drag reducers, embodiments of the present disclosure may allow comparisons of the magnitude of drag reduction across many samples. Increasing the number of samples may thereby allow an operator to determine type curves for each test, such that comparisons of different samples may be made across a matrix. The comparisons may then be used by an operator to select drag reducers having desirable properties, or to vary a quantity of drag reducer to achieve a desired response. Those of ordinary skill in the art will appreciate that the embodiments disclosed herein may be used to determine and or compare the properties of drag reducers, as may be found in any type of fluid stream. In still other embodiments, the methods and equipment disclosed herein may allow an operator to determine whether a drag reducer works, such that either a different drag reducer may be selected, or a property of the drag reducer adjusted.

While the disclosure has been described with respect to a limited number of embodiments, those skilled in the art, having benefit of this disclosure, will appreciate that other embodiments can be devised which do not depart from the scope of the disclosure as disclosed herein. Accordingly, the scope of the disclosure should be limited only by the attached claims.

What is claimed:

1. A system for screening a drag reduction agent, comprising:
   at least one pressure vessel, comprising:
      a first compressible container disposed in the at least one pressure vessel, the first compressible container having an outlet;
   a first tube fluidly connected with the outlet of the first compressible container;
   a second tube fluidly connected with the first tube;
   a timer; and
   a collection vessel configured to receive a fluid from the second tube.

2. The system of claim 1, wherein the pressure vessel comprises:
   a second compressible container, the second compressible container having a second container outlet.

3. The system of claim 2, wherein the first tube is fluidly connected with the outlet of the first compressible container and the second container outlet.

4. The system of claim 2, further comprising
   a third tube fluidly connected with the second container outlet; and
   a fourth tube fluidly connected with the third tube.

5. The system of claim 1, wherein the at least one pressure vessel comprises:
   a first pressure vessel, comprising:
      at least one container having an outlet; and
   a second pressure vessel, comprising:
      at least one container having an outlet.

6. The system of claim 5, further comprising
   a third tube fluidly connected with the outlet of the at least one container of the second pressure vessel; and
   a fourth tube fluidly connected with the third tube.

7. The system of claim 1, wherein the pressure vessel is fluidly connected to a pressurization source.

8. The system of claim 1, further comprising:
   a gauge, wherein the gauge comprises at least one of a pressure gauge and a temperature gauge; and
   wherein the gauge is connected to at least one of the pressure vessel, the first tube, and the second tube.

9. The system of claim 1, wherein the system further comprises:
   a weight sensor.

10. The system of claim 1, wherein the system further comprises:
    a programmable logic controller.

11. The system of claim 1, wherein a fluid in the system comprises at least one of water, a brine, a base oil, a drag reduction agent, and combinations thereof.

12. The system of claim 1, wherein a diameter of the second tube is less than a diameter of the first tube.

13. The system of claim 1, further comprising:
    a valve disposed between the first container and the first tube.

14. The system of claim 13, wherein the system further comprises:
    a switch, wherein the switch is configured to control the valve.

15. A method for measuring drag reduction of a fluid, the method comprising:
    pressurizing a pressure vessel, wherein the pressurizing comprises compressing at least one compressible container having the fluid therein;
    conveying the fluid through a first tube, wherein the first tube is in fluid communication with the at least one container;
    conveying the fluid though a second tube, wherein the second tube is in fluid communication with the first tube;
    collecting the fluid exiting the second tube in a collection vessel; and
    measuring a flow rate of the fluid through the first and second tube.

16. The method of claim 15, wherein the at least one container is flexible.

17. The method of claim 15, further comprising:
    measuring a temperature of the fluid.

18. The method of claim 15, further comprising:
    maintaining a constant temperature in at least one of the first tube, the second tube, the pressure vessel, and the at least one container.

19. The method of claim 15, further comprising:
    measuring a pressure in at least one of the first tube, the second tube, the pressure vessel, and the at least one container.

20. The method of claim 15, further comprising:
    maintaining a constant pressure in the pressure vessel.

21. The method of claim 15, wherein a diameter of the second tube is smaller than a diameter of the first tube.

22. The method of claim 15, wherein the conveying comprises inducing a turbulent flow in the fluid.

23. The method of claim 15, further comprising:
    weighing the fluid in the collection vessel.

* * * * *